US009509009B2

(12) United States Patent
Ulyanova et al.

(10) Patent No.: US 9,509,009 B2
(45) Date of Patent: Nov. 29, 2016

(54) ENZYME CATALYZED OXIDATION OF HYDROCARBONS

(71) Applicant: CFD Research Corporation, Huntsville, AL (US)

(72) Inventors: Yevgenia Ulyanova, Huntsville, AL (US); Shelley Minteer, Salt Lake City, UT (US); Sameer Singhal, Huntsville, AL (US); Vojtech Svoboda, Huntsville, AL (US); Jianjun Wei, Huntsville, AL (US)

(73) Assignee: CFD Research Corporation, Huntsville, AL (US)

( * ) Notice: Subject to any disclaimer, the term of this patent is extended or adjusted under 35 U.S.C. 154(b) by 88 days.

(21) Appl. No.: 14/261,797

(22) Filed: Apr. 25, 2014

(65) Prior Publication Data

US 2015/0050566 A1 Feb. 19, 2015

Related U.S. Application Data

(63) Continuation-in-part of application No. 14/198,035, filed on Mar. 5, 2014, which is a continuation of application No. 13/155,811, filed on Jun. 8, 2011, now Pat. No. 8,703,022.

(51) Int. Cl.
| | |
|---|---|
| C12M 1/00 | (2006.01) |
| H01M 8/16 | (2006.01) |
| C09D 11/52 | (2014.01) |
| C09D 11/04 | (2006.01) |
| B82Y 30/00 | (2011.01) |

(52) U.S. Cl.
CPC .............. *H01M 8/16* (2013.01); *C09D 11/04* (2013.01); *C09D 11/52* (2013.01); *B82Y 30/00* (2013.01)

(58) Field of Classification Search
CPC .......... H01M 4/86; H01M 4/90; H01M 4/96; H01M 8/16; H01B 1/20; G01N 33/487
USPC ..................................... 204/403.01; 429/401
See application file for complete search history.

(56) References Cited

U.S. PATENT DOCUMENTS

| | | | | |
|---|---|---|---|---|
| 7,638,228 B2* | 12/2009 | Minteer | ................ | C12N 11/08 427/115 |
| 8,415,059 B2* | 4/2013 | Minteer | ................ | C12N 11/04 429/401 |
| 2007/0131547 A1* | 6/2007 | Nomoto | ................ | C12Q 1/001 204/403.01 |
| 2011/0143225 A1* | 6/2011 | Nakagawa | .......... | H01M 4/8605 429/401 |

FOREIGN PATENT DOCUMENTS

GB 2341181 A * 3/2000 ............. C07C 29/48

* cited by examiner

*Primary Examiner* — Khanh Tuan Nguyen
(74) *Attorney, Agent, or Firm* — Jeremy A. Smith; Bradley Arant Boult Cummings LLP

(57) ABSTRACT

The present disclosure provides a method of generating electricity from a long chain hydrocarbon, said method comprising contacting the liquid non-polar substrate with a plurality of enzymes, wherein at least one enzyme is non-electric current/potential enzyme that functions as a catalyst for chemical reaction transforming a first substrate or byproduct to a second substance that can be used with an additional electric current/potential generating enzyme.

14 Claims, 13 Drawing Sheets

Depiction of Enzymatic Process for JP-8 conversion.

FIG. 2A and 2B
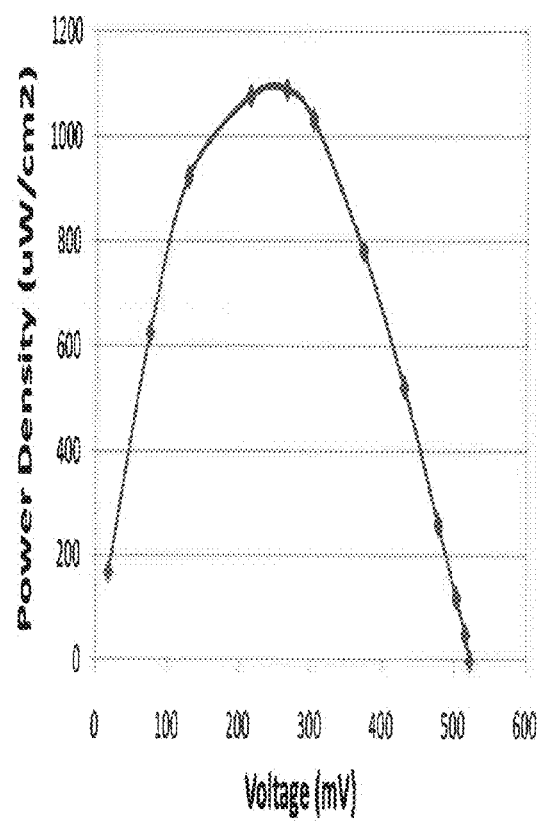
FIG. 2A
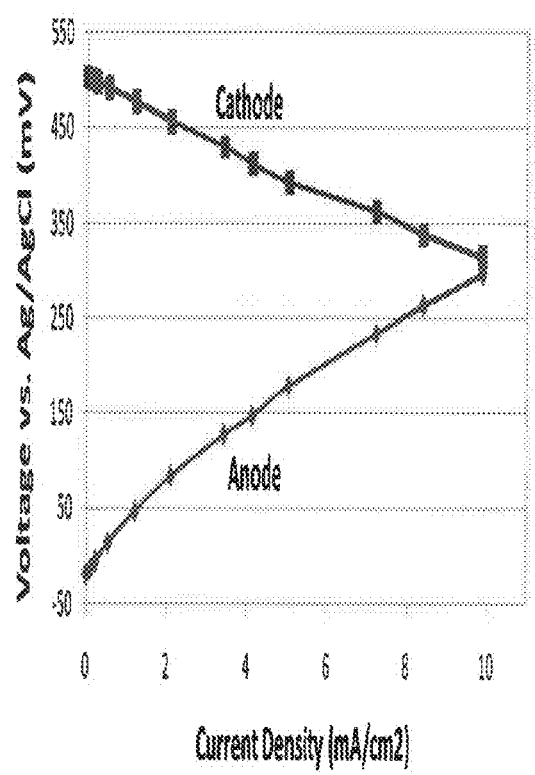
FIG. 2B

Figure 8: Depiction of Enzymatic Process for JP-8 conversion.

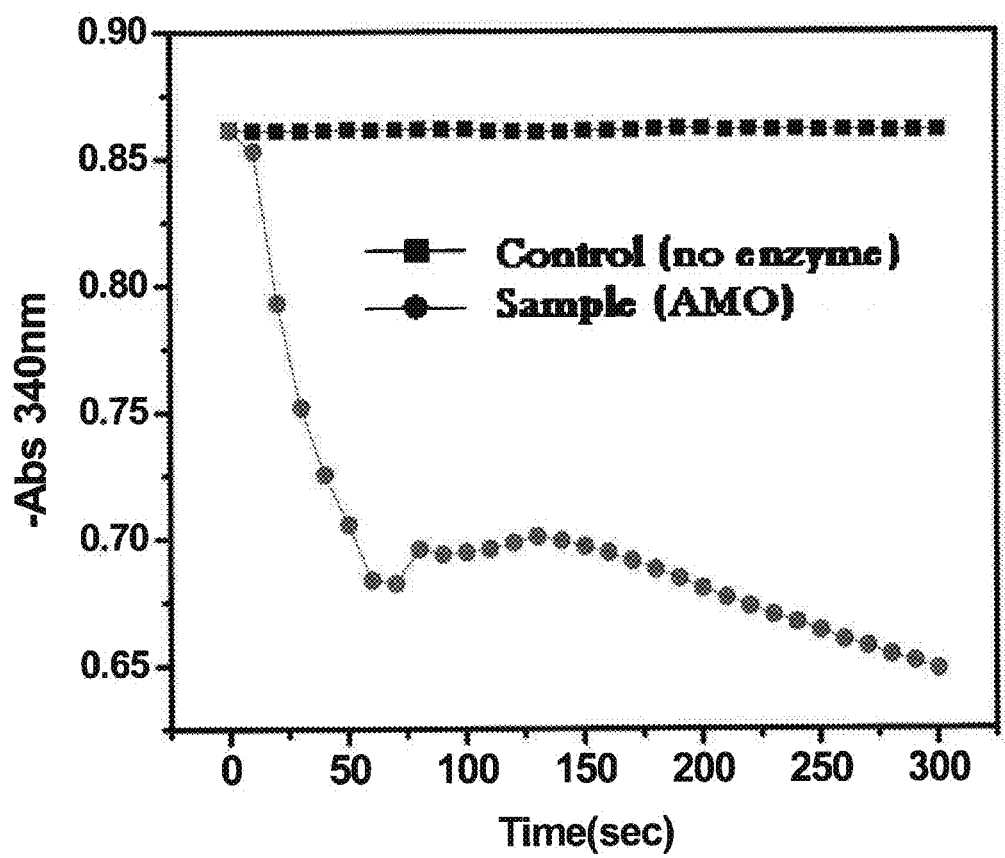
FIG. 9: UV-Vis spectroscopic assay testing of AMO activity towards octane as a substrate.

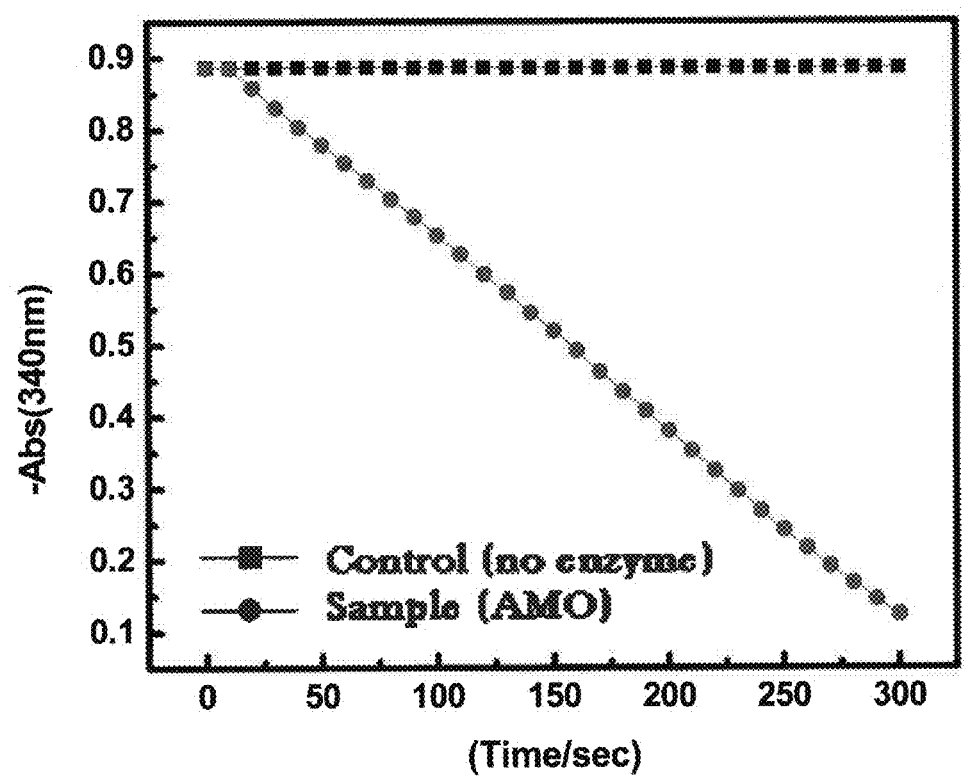
FIG. 10: UV-Vis spectroscopic assay testing of AMO activity towards hexane as a substrate.

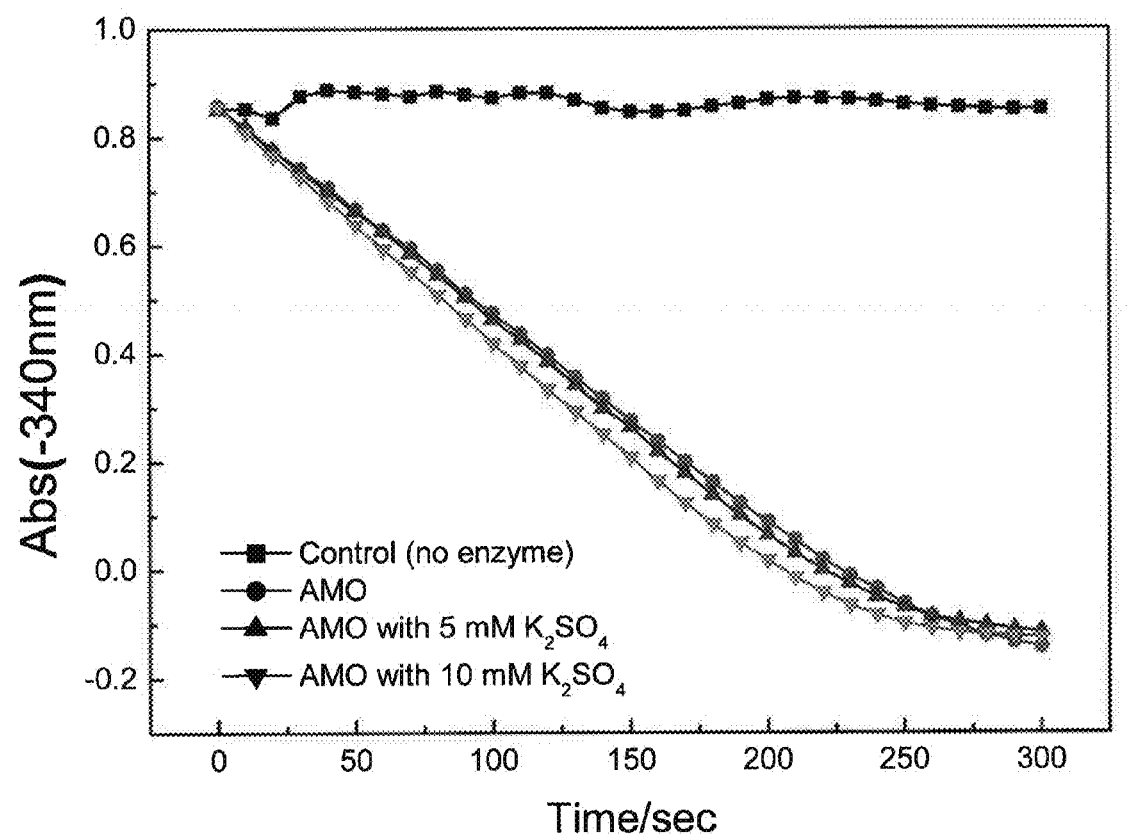
FIG. 11. UV-Vis spectroscopic assay testing of AMO to show sulfur tolerance.

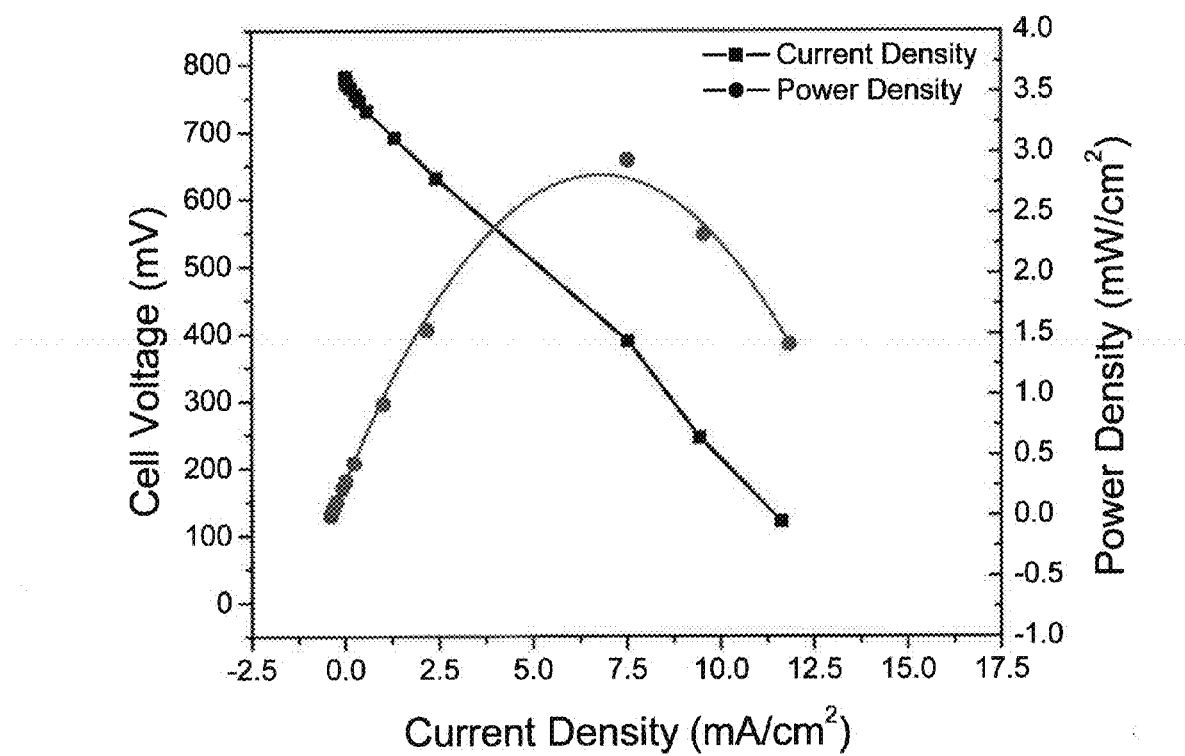
FIG. 12: Power and current density plot for bi-enzymatic fuel cell, tested with JP-8 as substrate.

ENZYME CATALYZED OXIDATION OF HYDROCARBONS

CROSS REFERENCE TO OTHER APPLICATIONS

This application is a continuation-in-part of and therefore claims priority to, and the benefit of, currently pending U.S. patent application Ser. No. 14/198,035 filed Mar. 5, 2014, entitled "Electrically Conductive Ink and Uses Thereof."

STATEMENT REGARDING FEDERALLY SPONSORED RESEARCH OR DEVELOPMENT

The research and inventions disclosed herein were funded at least in part by funds received from the U.S. Department of the Army pursuant to SBIR contract numbers W15P7T-06-C-T203 and W15P7T-09-C-S623. Accordingly, the United States government may have certain rights in this invention.

FIELD OF THE DISCLOSURE

The present disclosure pertains to the field of power generation. More specifically, the present disclosure pertains in part to an electrically conductive ink capable of operating at elevated temperatures. Uses of such electrically conductive inks and devices incorporating the same are also provided. Additionally, this disclosure pertains to the enzymatic oxidation of hydrocarbons (such as JP-8 fuel), fatty acids and their oxidation products.

BACKGROUND

Electrically conductive inks containing enzymes are known in the art. In many cases, these inks use either bio-molecules, such as enzymes, or even whole living organisms to catalyze oxidation of substrates, such as alcohols and carbohydrates to release electrons and generate electrical energy. Despite substantial research in the field, the prior art inks are often extremely difficult to reliably produce and are extremely temperature sensitive. These factors have restricted the use and applications of such electrically conductive inks. Therefore, the art is in need of improved electrically conductive inks with improved properties, such as, but not limited to, ease of manufacture and temperature stability.

Diesel fuels, including without limitation the "JP-X" fuels such as JP-4, JP-5 and JP-8, are some of the most common fuels used in military operations. Currently, the only way to convert these fuels into energy is through a combustion process. This process is inefficient and also has unwanted side effects such as toxic fumes and high noise signature. Similar kerosene fuels are very commonly used in domestic settings for running generators in remote locations or in disaster relief operations. Accordingly, there is a long-felt need for an apparatus and a method to electrochemically convert hydrocarbon fuels (such as JP-8 jet fuel) into energy. This electrochemical conversion has higher efficiency with no thermal or acoustic signature or toxic by-products. Electrochemical methods have long been explored using metal catalyzed fuel cells, but the metal catalysts are poisoned by the high sulfur content of many fuels thus the current methods require a costly reforming or purification step prior to electrochemical synthesis.

The present disclosure provides a solution to this long-felt need. The present disclosure provides an improved apparatus and method for the electrochemical conversion of hydrocarbon fuels (such as JP-8 jet fuel) into energy using enzymes as catalysts. Such a novel feature has not been previously disclosed in the art.

BRIEF DESCRIPTION OF THE DRAWINGS

FIGS. 2A and 2B show a graph of power density vs. voltage of one embodiment of the ink used in a fuel cell.

FIG. 9 shows the catalytic activity of the enzyme alkane monooxygenase (AMO) towards alkanes.

FIG. 10 shows the catalytic activity of AMO towards hexane as a substrate.

FIG. 11 shows the tolerance of the AMO enzyme to sulphur.

FIG. 12 shows a power and density plot for one embodiment of a bi-enzymatic fuel cell with JP-8 fuel as the substrate as disclosed herein.

SUMMARY OF THE DISCLOSURE

Figure 1:
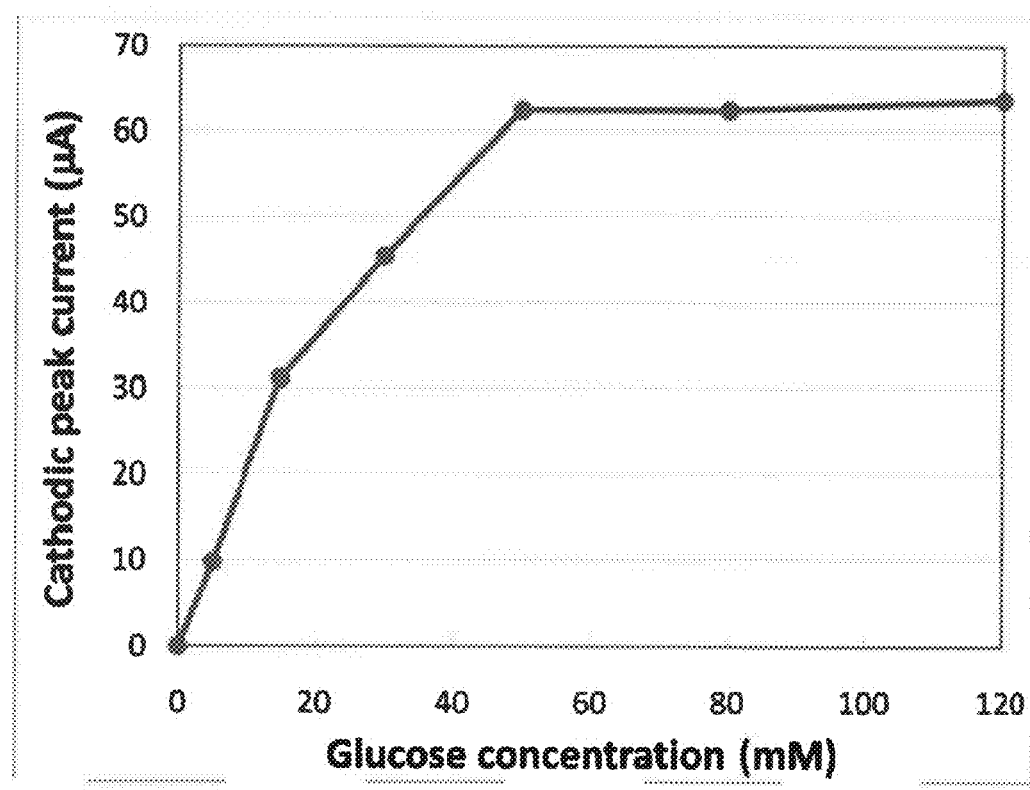
FIG. 1 shows one embodiment of the ink and the anodic current dependence thereof on increasing glucose concentrations.

In a first aspect, the present disclosure provides an electrically conductive ink exhibiting superior retention of electrical conductivity and biocatalytic activity of immobilized enzymes at elevated temperatures. In one embodiment of this aspect, the electrically conductive ink consists of, consists essentially of or comprises a nano-scale conducting material, a binding agent and one or more enzymes, and is essentially solvent free. The electrically conductive ink may further comprise additional components, including, but not limited to, a mediator and a cross-linking agent. In a second aspect, the present disclosure provides an aqueous based electrically conductive ink consisting of, consisting essentially of or comprising a nano-scale conducting material, a binding agent and one or more enzymes, wherein the ink is essentially solvent free. The electrically conductive ink may further comprise additional components, including, but not limited to, a mediator and a cross-linking agent. In a particular embodiment, the electrically conductive ink exhibits superior retention of electrical conductivity and biocatalytic activity at elevated temperatures.

In a third aspect, the present disclosure provides an electrically conductive ink, existing in a first form and a second form, wherein the first form is a water-soluble aqueous based solution which consists of, consists essentially of or comprises a nano-scale conducting material, a binding agent, an aqueous buffer and one or more enzymes and the second water insoluble form is generated from the first form and consists of, consists essentially of or comprises the nano-scale conducting material, the binding agent and the one or more enzymes. The electrically conductive ink, in either or both of the first or second forms, may further comprise additional components, including, but not limited to, a mediator and a cross-linking agent. Furthermore, the electrically conducting ink may be essentially solvent free. In one embodiment of this aspect, the electrically conductive ink exhibits superior retention of electrical conductivity and biocatalytic activity at elevated temperatures and is essentially solvent free.

In a fourth aspect, the present disclosure provides a fuel cell comprising an electrode material, the electrode material further comprising an electrically conductive ink of the first through third embodiments deposited on said electrode.

In a fifth aspect, the present disclosure provides an apparatus and a method for the enzymatic oxidation of hydrocarbons such as diesel fuel, kerosene and others.

DETAILED DESCRIPTION

Composition

In one embodiment, the present disclosure provides an electrically conductive ink exhibiting superior retention of electrical conductivity and biocatalytic activity at elevated temperatures. In one embodiment of this aspect, the electrically conductive ink consists of, consists essentially of or comprises at least one of a nano-scale conducting material, a binding agent and one or more enzymes, and is essentially solvent free. The electrically conductive ink may further comprise additional components, including, but not limited to, a mediator and a cross-linking agent.

In another embodiment, the present disclosure provides an aqueous based electrically conductive ink consisting of, consisting essentially of or comprising a nano-scale conducting material, a binding agent and one or more enzymes, wherein the ink is essentially solvent free. The electrically conductive ink may further comprise additional components, including, but not limited to, a mediator and a cross-linking agent. In a particular embodiment, the electrically conductive ink exhibits superior retention of electrical conductivity and biocatalytic activity at elevated temperatures.

In still a further embodiment, the present disclosure provides an electrically conductive ink, existing in a first form and a second form, wherein the first form is a water-soluble aqueous based solution which consists of, consists essentially of or comprises a nano-scale conducting material, a binding agent, an aqueous buffer and one or more enzymes and the second water insoluble form is generated from the first form and consists of, consists essentially of or comprises the nano-scale conducting material, the binding agent and the one or more enzymes. The electrically conductive ink, in either or both of the first or second forms, may further comprise additional components, including, but not limited to, a mediator and a cross-linking agent. Furthermore, the electrically conducting ink may be essentially solvent free. In a specific embodiment, the electrically conductive ink exhibits superior retention of electrical conductivity and biocatalytic activity at elevated temperatures and is essentially solvent free.

In a specific embodiment, the electrically conductive inks described above incorporate a cross-linking agent. In a further specific embodiment, the electrically conductive inks described above incorporate a mediator. In still a further embodiment, the electrically conductive inks described above incorporate a cross-linking agent and a mediator.

In embodiments of the foregoing where the mediator is not present in the electrically conductive ink, the mediator may be present in a fluid solution surrounding the electrically conductive ink. In one embodiment, the mediator is present in a fluid solution surrounding the electrically conductive ink.

In this embodiment, the first form of the electrically conductive ink of the present disclosure is characterized as a water-soluble aqueous based solution consisting of, consisting essentially of or comprising: a nano-scale conducting material, a binding agent, an aqueous buffer and one or more enzymes. The first form may further comprise a mediator and a cross-linking agent. The second form of the electrically conductive ink is characterized as a water insoluble matrix consisting of, consisting essentially of or comprising the nano-scale conducting material, the binding agent and the one or more enzymes. In this embodiment, the second form may be generated from the first form by curing the ink for a period of time. Other methods known in the art may also be used. In one embodiment, the second form is generated from the first form by self curing the electrically conductive ink on a conductive electrode surface at about 4 degrees Celsius. The first form and or the second form may further comprise a mediator and a cross-linking agent.

In the embodiments of the electrically conductive ink described herein, the electrically conductive ink exhibits increased retention of electrical conductivity and biocatalytic activity at increased temperatures when compared to prior art electrically conductive inks. For example, the electrically conductive ink retains significant electrical conductivity and biocatalytic activity at temperatures above 40 degrees Celsius or above 50 degrees Celsius as compared to prior art ink. In a particular embodiment, the electrically conductive inks of the present disclosure retain 75%, 80%, 85%, 90%, 95%, or greater of their electrical conductivity and biocatalytic activity while operating or being stored at increased temperatures (such as over 40 and 55 degrees Celsius) as compared to 22 degrees Celsius.

In the embodiments of the electrically conductive ink, including the first and second forms thereof, described herein the electrically conductive ink incorporates a nano-scale conducting material. In one embodiment, the first form and second form of the electrically conductive ink comprises a nano-scale conducting material. The nano-scale conducting material may serve several functions including, but not limited to, providing a large surface area to volume for charge transfer rations that increase the electrode's total biocatalytic reaction rates, immobilizing and stabilizing the enzyme, and facilitating efficient electron transfer from the enzyme directly to the cathode or anode, or from the enzyme to the mediator and from mediator to cathode or anode. In one embodiment, the nano-scale conducting material is a carbon nanotube (CNT). CNTs are sheets of graphitic carbon, rolled into a cylinder (or tube) shape that have remarkable electronic properties and many other unique characteristics. In yet a further embodiment of the present disclosure, the CNT may either be a single walled or multi-walled CNT. Single walled CNTs comprise a single rolled layer of graphite carbon while multi-walled CNTs comprise multiple rolled layers (or concentric tubes) of graphite. In yet a further embodiment, the single- or multi-walled CNT may be functionalized. Functionalized CNTs have additional chemical molecules or functional groups attached to their sidewalls and display increased solubility in aqueous solutions and polymer resins as compared to non-functionalized CNTs. In one further embodiment, the CNT has been functionalized by the addition of a carboxylic acid (COOH) group, however functionalization with other groups including without limitation hydroxyl (OH), amines (NH2), bromine (Br), and others including larger biomolecules are possible and should be considered within the scope of this invention.

In the embodiments of the electrically conductive ink, including the first and second forms thereof, described herein the electrically conductive ink incorporates a binding agent. The binding agent is miscible or soluble in aqueous solutions. The binding agent serves to immobilize the nanoscale conductive material, the one or more enzymes and other components of the ink. The binding agent may be any suitable agent as selected by one skilled in the art and may include polymers and other suitable compounds. In one embodiment, the water miscible binding agent is polymer. In one embodiment, the polymer is a cationic polymer, such as, but not limited to, polyethyleneimine (PEI) polymer. In an alternate embodiment, the cationic polymer is selected from the following group: poly[α-(4-aminobutyl)-L-glycolic acid], polyesters, poly(4-hydroxy-1-proline ester), poly(β-aminoesters), poly-(L-lactide-co-L-lysine), poly(amidoamine) dendrimers, poly(serine ester), poly(lysine), lypopolyamines, polybrene, polyamine, DEAE-dextran, polyamidoamines and co-polymers made from at least one of the forgoing. In an alternate embodiment, the ink may comprise one of the following binding agents: chitosan, polyarylene ether with quaternary ammoniun salts, Lead selenide (PbSe), polybidphenol A-co-epichlorohydrin (BAEH), polystyrene-b-polyethylene oxide, polyethyleneoxide, polysulfones or Nafion.

In the embodiments of the first form of the electrically conductive ink described herein the electrically conductive ink incorporates an aqueous buffer. In one embodiment, the aqueous buffer is potassium phosphate buffered saline (PBS) of concentration range of 5 mM to 1M. In alternate embodiments, the aqueous buffer may be (4-(2-hydroxyethyl)-1-piperazineethanesulfonic acid) (HEPES), N-Tris(hydroxymethyl)methyl-3-aminopropanesulfonic Acid (TAPS), N,N-Bis(2-hydroxyethyl)glycine (Bicine), (hydroxymethyl)aminomethane (TRIS), N-[Tris(hydroxymethyl)methyl]glycine, 3-[(3-Cholamidopropyl)dimethylammonio]propanesulfonic acid (Tricine), N-Tris(hydroxymethyl)methyl-2-aminoethanesulfonic Acid (TES), 3-(N-morpholino)propanesulfonic acid (MOPS), 2-[4-(2-sulfoethyl)piperazin-1-yl]ethanesulfonic acid (PIPES), 2-(N-morpholino)ethanesulfonic acid (MES), potassium phosphate, sodium phosphate or cacodylate.

In the embodiments of the electrically conductive ink, including the first and second forms thereof, described herein the electrically conductive ink incorporates an enzyme. In certain embodiments, more than one enzyme may be present. In one embodiment the enzyme may be a single oxidoreductase enzyme capable of oxidizing or reducing a substrate to release or consume electrons which may then be used to create an electric potential/current. As is known to those skilled in the art, oxidoreductase enzymes may be oxidases, dehydrogenases or hydrogenases. In one embodiment, the oxidoreductase enzyme is an oxidase which is capable of oxidizing a carbohydrate substrate. By way of non-limiting example, in one particular embodiment the oxidase enzyme may glucose oxidase. In yet a further embodiment, the oxidoreductase enzyme may be dehydrogenase such as pyrrolo-quinoline-quinone (PQQ) glucose dehydrogenase, D-fructose-5-dehydrogenase, glucose dehydrogenase, alcohol dehydrogenase, gluconate 2-dehydrogenase, laccase, bilirubin oxidase, ascorbate oxidase, aldehyde dehydrogenase, oxalate oxidase, malate dehydrogenase, succinate dehydrogenase, pyruvate dehydrogenase, glutamate dehydrogenase, isocitrate dehydrogenase, alkane monooxygenase, alcohol oxidase, lactate oxidase, glycerol dehydrogenase, glycerol oxidase, trehalase or lactate dehydrogenase. As will be realized by one skilled in the art, the choice of one or more enzymes may be influenced by the substrate upon which the one or more enzymes act, the availability of substrate and other concerns such as the desired operating environment of the electrically conductive ink.

In one embodiment of the present disclosure, the substrate may be a simple or complex carbohydrate, such as, but not limited to, glucose, fructose, sucrose, trehalose, or an alcohol, such as, but not limited to, glycerol, methanol or ethanol. Other substrates include ethylene glycol, diethylene glycol, polyethylene glycol, diol, potentially cellulose, JP-8 fuel, JP-5 fuel, propane, hexane octane, JP-4 fuel, diesel fuel, methane, butane, long chain hydrocarbon, kerosene or a non-polar chemical. In one embodiment, the substrate may comprise sulphur. The substrate may comprise up to between 1 ppm and 10,000 ppm sulphur, 1 ppm and 5,000 ppm sulphur, between 1 ppm and 1,000 ppm sulphur and 1 ppm and 500 ppm sulphur. In an alternate embodiment, the substrate comprises between 100 ppm and 10,000 ppm sulphur and in a preferred embodiment comprises between 100 ppm and 5,000 ppm sulphur.

In a preferred embodiment where the substrate comprises at least in part a long chain hydrocarbon, a fuel or other non-polar chemical, phase separation between the non-polar substrate and the aqueous electrolyte can be problematic. Accordingly, it may be desirable to employ a method for breaking the long chain hydrocarbon into shorter chain hydrocarbons which are more soluble in water. The hydrocarbons may be "broken" by either an enzymatic or physical means. In one embodiment, a class of enzymes known as lyases may be added to the substrate to cleave the C—C bonds present in the substrate.

In yet an alternate embodiment of the present invention, the electrically conductive ink may contain two or more enzymes. In one embodiment, the two or more enzymes may be part of an enzyme cascade. Enzymes that are capable of releasing or consuming a proton/electron in oxidation or reduction reaction respectively generate an electric current/potential. An enzyme cascade might also contain non-electric current/potential enzymes that function as catalysts for chemical reaction, transforming a first substrate or byproduct to a second substance that can be used with the electric current/potential generating enzymes. In one embodiment, the two or more enzymes may both be electric current/potential generating enzymes and may be selected so that the reaction product of one enzymatic reaction may be the substrate for the other enzymatic reaction. As those skilled in the art will realize, and by way of non-limiting example, the two or more enzymes may include two enzymes selected from the enzymes involved in the Kreb's Cycle (also known as the citric acid cycle) involved in aerobic respiration or invertase (also known as sucrase) and glucose oxidase for the hydrolysis of sucrose or alcohol oxidation cascades used in fermentation.

In a preferred embodiment, the first enzyme may be alkane monooxygenase (AMO) which catalyzes a chemical reaction of an alkane to an alcohol. In an alternate preferred embodiment, the first enzyme may be selected from the group consisting of alkane hydroxylases, membrane-bound particulate copper-containing enzymes (pMMO), soluble non-heme di-iron monooxygenases (sMMO, which is generally comprised of a hydroxylase and a reductase), and cytochrome P450 enzymes. Further in a preferred embodiment, the second enzyme may be alcohol oxidase which further catalyzes the oxidation of the alcohol, produced from the AMO reaction, to an aldehyde. In other preferred embodiments, the second enzyme may be alcohol dehydrogenase, aldehyde dehydrogenase, aldehyde oxidase or other suitable enzymes which can release electrons from an alcohol.

In the embodiments of the electrically conductive ink, including the first and second forms thereof, described herein the electrically conductive ink incorporates a mediator. The mediator may be any compound that can assist in the transfer of electrons from the enzyme to the nano-scale conductive material and conductive electrode surface or which can directly or indirectly increase the efficiency of the oxidation of the substrate by the one or more enzymes. In one embodiment, the mediator may be hydroquinone (HQ), ferrocene or ferricyanide. In yet another embodiment, the mediator may be an osmium containing compound. In yet an alternate embodiment, the mediator may be an azine containing compound such as methylene blue or methylene green. In yet another alternate embodiment, the mediator may be flavin adenine dinucleotide (FAD), nicotinamide adenine dinucleotide (NAD), nicotinamide adenine dinucleotide phosphate (NADP), pyrrolo-quinoline-quinone (PQQ), NADH, TTF or osmium, ruthenium, or ferrocene based redox polymers. As known to those skilled in the art, the selection of mediator will be influenced by the one or more enzymes present in the electrically conductive ink and the substrate upon which those enzymes act.

In the embodiments of the electrically conductive ink, including the first and second forms thereof, described herein the electrically conductive ink incorporates a cross-linking agent. The cross-linking agent functions to assist the transition of the first form of the electrically conductive into the second form. As known to those skilled in the art, the selection of cross-linker may be dependent upon the selection of the binding agent or one or more enzymes and other factors. By way of non-limiting example, the cross-linker may be 1-Ethyl-3-[3-dimethylaminopropyl]carbodiimide hydrochloride (EDC), a N-hydroxy succinimide (NHS) ester, lysozyme, Dithiobis[succinimidyl propionate (DSP), dithiobis(N-succinimidyl propionate) (DTSP) and potentially others. In one embodiment, the cross-linking agent is EDC, NHS or a combination of the two.

In yet another embodiment, the electrically conductive ink further comprises a monomer of an electrically conductive polymer and an electrolyte. The electrically conductive polymer may be polypyrrole (PPY), polyaniline (PANI), polyacetylene (PAC), poly(p-phenylene vinylene) (PPV) or any other suitable polymer known to those of skill in the art. A wide selection of electrolytes including ionic liquids might be used. The polymerization reaction might be facilitated with electropolymerization, chemical polymerization, or be also catalyzed with enzymes. In one preferred embodiment, lithium perchlorate ($LiClO_4$) is the electrolyte. As known to those skilled in the art, the selection of monomer of an electrically conductive polymer and an electrolyte may be dependent upon the selection of the one or more enzymes and other factors. By way of non-limiting example, the monomer of an electrically conductive polymer may be electrically polymerized pyrrole or aniline while the electrolyte comprises lithium perchlorate.

In a specific embodiment of the foregoing, the electrically conductive ink consists of, consists essentially of or comprises CNTs as the nano-scale conducting material, a binding agent, a cross-linking agent and an enzyme. The CNTs may be single walled or multi-walled and may be functionalized with chemical molecules or functional groups attached thereto. In one embodiment, the CNT is a single wall CNT with COOH functional groups attached thereto. In such an embodiment, the enzyme, binding agent and cross-linking agent may be selected from those described herein. In one further embodiment of the foregoing, the enzyme is glucose oxidase, the binding agent is PEI and the cross-linking agent is a combination of EDC and NHS. Furthermore, the ink may be essentially solvent free.

Uses

The electrically conductive ink of the present disclosure has many uses. For example, the electrically conductive ink may be used as part of an electrode. The electrode may be used in a diverse range of applications, such as, for example, the construction of a fuel cell, a battery electrode or a sensor electrode. The fuel cell then may be used for powering remote monitors, surveillance devices, sensors (such as sensors capable of detecting chemical and/or biological warfare agents), in implantable medical devices or in the field as part of a battery recharging device to recharge batteries in crucial operations (such as on the battlefield by soldiers) when there is no supply electrical power, but a substrate source is available.

The fuel cell in one embodiment of the present disclosure uses the electrode comprising the electrically conductive ink as at least one of an anode or a cathode. In one embodiment, the electrode can be made into a plate-like or layer-like form, and used in a single layer. The fuel cell can include a reaction vessel capable of storing substrate and an anode and a cathode arranged in the reaction vessel, and the fuel cell electrode according to the present disclosure is used for at least one of the anode or the cathode. In one embodiment, the fuel cell electrode comprises a carbon-based electrode paper, such as Toray paper, glassy carbon, planar gold surface, gold nanostructured surfaces, gold wire, carbon coated wire or carbon microfibers upon which the ink is deposited. In one embodiment, the carbon-based electrode paper comprises the anode of the fuel cell which is separated by a sulfonated tetrafluoroethylene based fluoropolymer-copolymer membrane, such as Nafion® (or any such other suitable proton conductive material) from the fuel cell's cathode. In one embodiment, the cathode is an oxygen reduction cathode that can be designed for an air breathing operation. In one embodiment, the oxygen reduction reaction in the cathode might be catalyzed by platinum (Pt), other metals, or a combination thereof, an inorganic catalyst, or by bioelectrocatalysts like laccase, bilirubin oxidase, ascorbate oxidase and other enzymes. The cathode may comprise various chemistries that provide reduction reactions in which protons and electrons are consumed.

The enzymatic oxidation of hydrocarbons disclosed herein likewise has many potential uses including providing a renewable energy source suitable for providing power in remote areas or in military applications. Additional uses include sensing of hydrocarbons or processing of fuels to go from gaseous form to liquid fuels for transportation.

Advantages

The electrically conductive ink of the present disclosure has many surprising characteristics as compared to the known art. First, as discussed in Examples 3 and 7 shown by FIGS. 3A, 3B, 7A and 7B, the electrically conductive ink renders the one or more enzymes and other components of the ink much less sensitive to elevated temperatures (and long term storage at elevated temperatures) than the native enzyme and other electrically conductive inks of the prior art. This characteristic provides the ability for the electrically conductive ink, and devices incorporating the same, to be operable over a wider range of conditions than was previously possible. In addition, the electrically conductive ink of the present disclosure and devices incorporating the same can be stored under conditions that would inactivate prior art electrically conducting inks and devices depending on such inks, greatly simplifying use in real-world conditions. As shown by Examples 3 and 7, the electrically conductive ink retains conductivity and biocatalytic activity and the ability to produce electrical power after storage at an elevated temperature as compared to native enzyme. Further, a fuel cell comprising an electrode upon which the electrically conductive ink has been deposited is environmentally friendly as compared to traditional batteries and fuel cells. Finally, the theoretical energy density of a fuel cell comprising an electrode upon which the electrically conductive ink has been deposited is approximately ten (10) times greater than lithium-ion batteries. Recent developments have allowed the further adaption and demonstration of a "Bio-Battery" as disclosed and claimed herein by implementing a cascade of enzymes capable of electrochemically converting JP-8 jet fuel directly into electrical energy. This technology has significant advantages over existing generators used to convert JP-8 into energy. Namely the energy generation process is silent and occurs under ambient conditions while producing >2× the efficiency. The "Bio-Battery" also has advantages over traditional fuel cell technologies which use metal catalysts that are susceptible to sulfur poisoning and thus require the JP-8 to be reformed prior to use. The enzyme catalysts reported here are naturally sulfur tolerant, allowing the use of JP-8 in its native form

EXAMPLES

Example 1

To demonstrate the functionality of the electrically conductive ink of the present disclosure, the ability of the electrically conductive ink to generate electrical current was tested. In this example, the electrically conductive ink comprised single wall COOH functionalized CNTs as the nanoscale conducting material, PEI as the binding agent, and glucose oxidase as the enzyme. To create the electrically conductive ink, the polymer was dissolved in a phosphate buffer solution by stirring in a ratio of 100-2000 μg/mL for several hours. After the solution was sufficiently mixed, CNTs were added to the mixture. In this example, single-walled CNTs with COOH functionalization were utilized. The CNT ratio was between 1-50 mg/mL and the mixing was accomplished via sonication with an ultrasonicator. Next, the enzyme and cross-linking agents are added to the solution. In this example, the cross linkers EDC and NHS were added along with the enzyme glucose oxidase. To construct the electrode, a small volume of the electrically conductive ink solution was pippetted onto a Toray paper electrode material. The electrode was allowed to cure overnight at approximately 4° Celsius.

The following day, the Toray paper electrode was rinsed with phosphate buffer solution and then attached to a standard glassy carbon electrode for testing in 3-electrode cyclic voltametry (CV) test. In this test the electrode comprising the electrically conductive ink serves as the working electrode, with an Ag/AgCl (3M KCl) reference electrode and a platinum counter electrode. CV tests were performed from −0.8V to +0.8V with a scan rate of 10 mV/s. In order to test for biocatalytic activity of the enzyme immobilized in the ink, CV sweeps were done with increasing glucose concentrations of 0, 5, 15, 30, 50, 80, and 120 mM in a test solution of 245 mM phosphate buffer solution with 10 mM HQ added as an electron mediator. FIG. 1 shows anodic current dependence on glucose concentration (i.e., the current increases as the glucose concentration is increased). This test demonstrates the ability of the electrically conductive ink to oxidize glucose and produce electrical current. For reference, a blank piece of Toray paper was also tested under the same conditions and showed no increase in current with adding glucose.

Example 2

In order to demonstrate power generation, the electrode described in Example 1 was combined with a Pt-based oxygen reduction cathode in a fuel cell test configuration. In this example, the electrically conductive ink was prepared using the same procedure as in Example 1 and then drop casted onto a carbon felt based electrode. This electrode was loaded into a custom designed polycarbonate based fuel cell test assembly as the anode side of the fuel cell. For the cathode side of the device a Pt-based half-MEA consisting of 0.5 mg/cm$^2$ Pt on a gas diffusion electrode hot pressed to a Nafion 117 membrane was used. The substrate (serving as the "fuel") comprised 50 mM glucose in 245 mM phosphate buffer solution with 10 mM HQ used as a mediator to improve electron transport. Power generation was tested by placing the fuel cell under constant load and measuring the resultant voltage and current across that load. The load was varied in steps from an open circuit condition (5 M-ohms) to a high electric loading condition (10 ohms). The maximum power was at ~500 ohms with a voltage of 0.3 V, current of 2.5 mA·cm$^{-2}$ and total power of 1 mW·cm$^{-2}$ as shown in FIGS. 2A and 2B.

Example 3

Figures 3A, 3B:
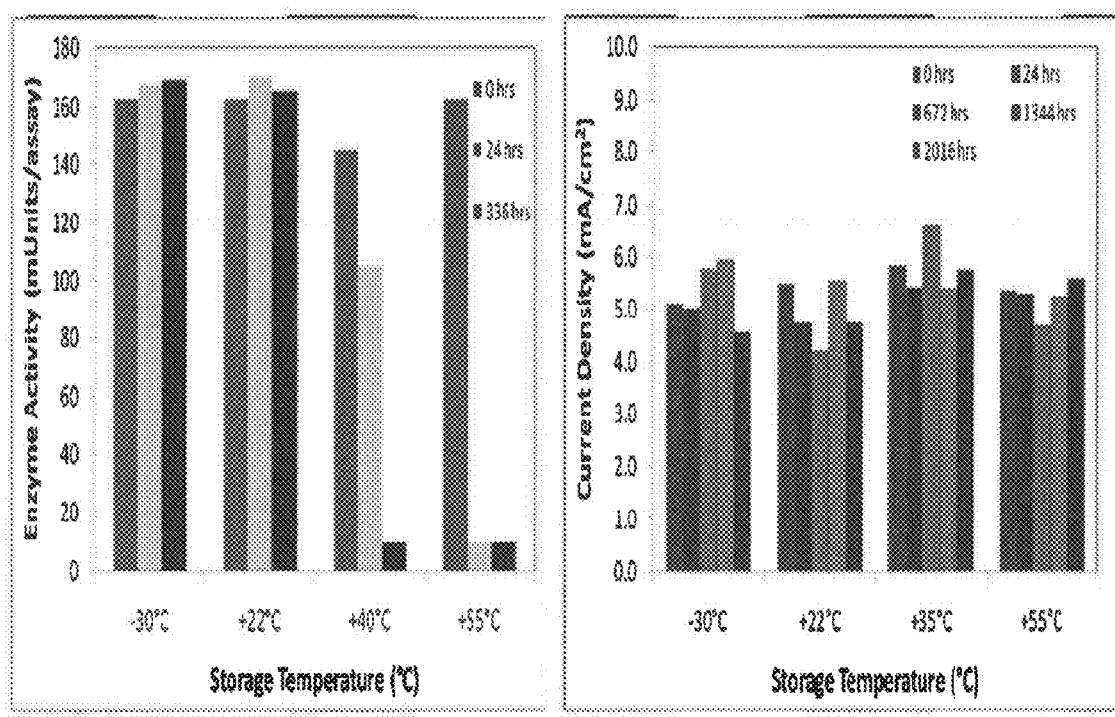
FIGS. 3A and 3B show the activity of the enzyme at increasing temperatures in free solution and electrical current produced for one embodiment of the ink used in a fuel cell.

In order to demonstrate the stability of the ink at elevated temperatures during storage, the ink was stored at elevated temperatures for extended periods of time. As a control experiment, the glucose oxidase enzyme was mixed in aqueous buffer solution and stored at temperatures of −30° C., +22° C., +40° C., and +55° C. A standard enzyme activity assay (Megazyme) was used to measure the activity of the enzyme after various storage intervals. The results shown in FIG. 3A establish that the free enzyme lost enzymatic activity after 24 hrs at +40° C. and almost immediately at +55° C. As a comparison, testing was performed on electrodes prepared with the enzymatic ink process. The electrodes were created using the same electrode preparation and fuel cell test procedure described in Examples 1 and 2. Multiple electrodes were prepared and tested. Electrodes were then stored at temperatures of −30° C., +22° C., +35° C., +55° C., and +70° C. with three electrodes being stored at each condition. The electrodes were tested at periodic intervals up to 3 months. The electrical testing consisted of measurement of current density at a constant resistance of 10 Ohms. The electrical testing was used in lieu of the standard assay testing as the immobilized electrode was not compatible with standard assay techniques. However, the ability to generate electrical current is dependent of the enzymatic oxidation of the glucose substrate and is definitive evidence that the enzymes are still active. The results in FIG. 3B show significant current generation and no degradation in performance after storage of up to +55° C. The novel formulation of the electrically conductive ink of the present disclosure provides for stabilization of the enzymes contained therein and allows the electrically conductive ink to function at elevated temperatures.

Example 4

Figures 4A, 4B:
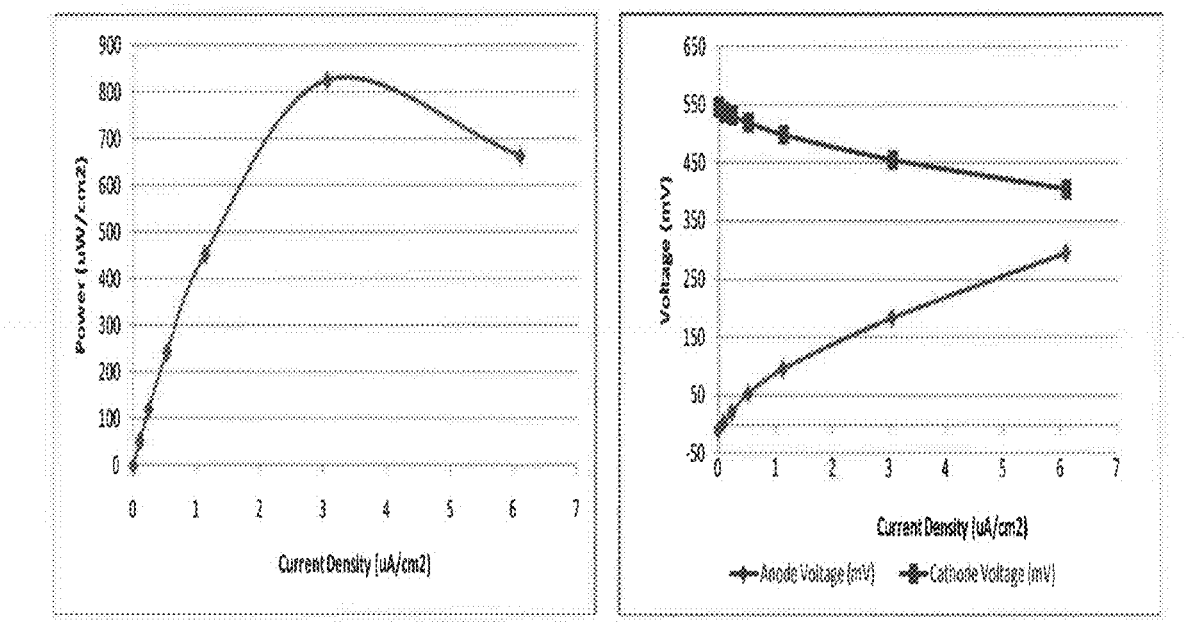
FIGS. 4A and 4B show the power curve of a cell and polarization curves of cathode and enzymatic anode with one embodiment of the ink in combination with a conductive polymer.

As shown in this example, in one embodiment adding a conductive polymer to the ink improves electrical conductivity and also improves mechanical stability and properties of ink layer. We added into the ink 1-30% by volume to the following pyrrole solution: 5-100 mM pyrrole with 10-500 mM $LiClO_4$ mixed in 20-300 mM PBS pH7. After deposition and before the anode testing, pyrrole monomer additive in the deposited ink layer is electrochemically polymerized for 5-50 seconds at +0.2-1.2 V vs. Ag/AgCl. Anodes fabricated with the addition of the conductive polymer (polypyrrole) were assembled into a fuel cell with air-breathing Pt cathode as described in Example 2. Results from this test are shown in FIGS. 4A and 4B showing >800 $\mu W \cdot cm^{-2}$ at current >3 $mA \cdot cm^{-2}$.

Example 5

Figures 5A, 5B:
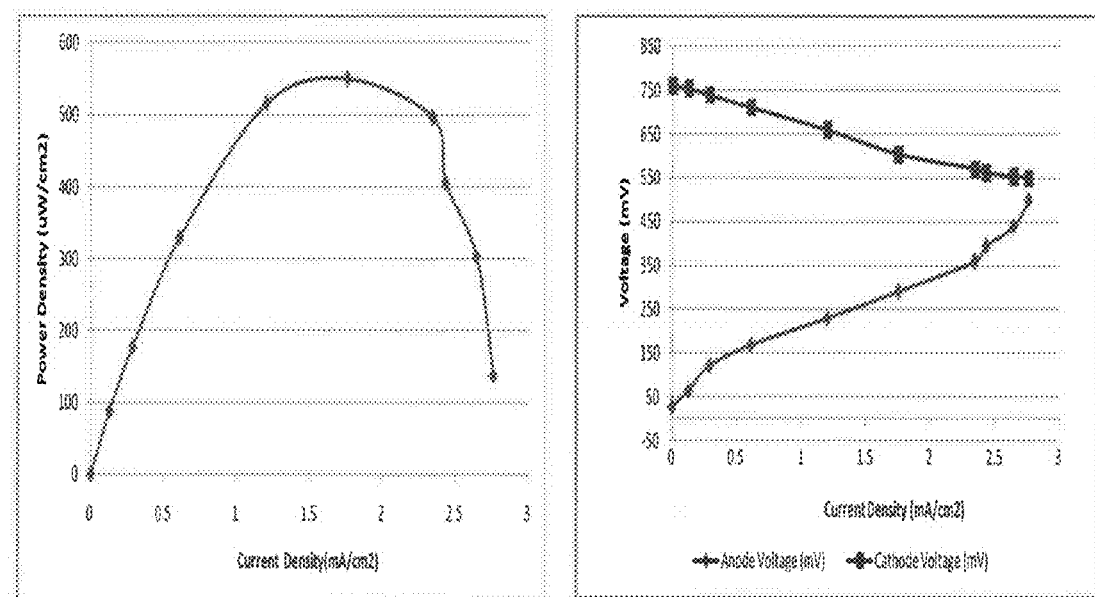
FIGS. 5A and 5B show the power curve of a cell and polarization curves of cathode and enzymatic anode with one embodiment of the ink in combination with a Tetrathiafulvalene (TTF) mediator.

As shown in this example, in one embodiment adding an electron mediator to the ink provides immobilized mediator. The specific mediator used in this example was TTF. A solution of TTF and acetone was mixed and the CNTs were dispersed in this solution. The TTF-CNT solution was centrifuged and decanted several times and then the supernatant solution was mixed with binding agent (PEI), enzyme (glucose oxidase), and cross-linkers (EDC and NHS) as before to make an ink solution. The ink solution was deposited on to a Toray Paper based electrode (anode) which was combined with Pt air-breathing cathode and FC hardware as described in Example 2. The incorporation of the TTF allows for the removal of the diffusive HQ mediator used in Example 2 and the fuel consisted strictly of glucose and buffer solution (50 mM glucose and 245 mM PBS). The test procedure was as described in Example 2. Results in FIGS. 5A and 5B clearly showed enzymatic activity and mediated electron transfer with immobilized mediator in the ink with power density of >500 $\mu W \cdot cm^{-2}$ generated at current >1.5 $mA \cdot cm^{-2}$.

Example 6

Figure 6:
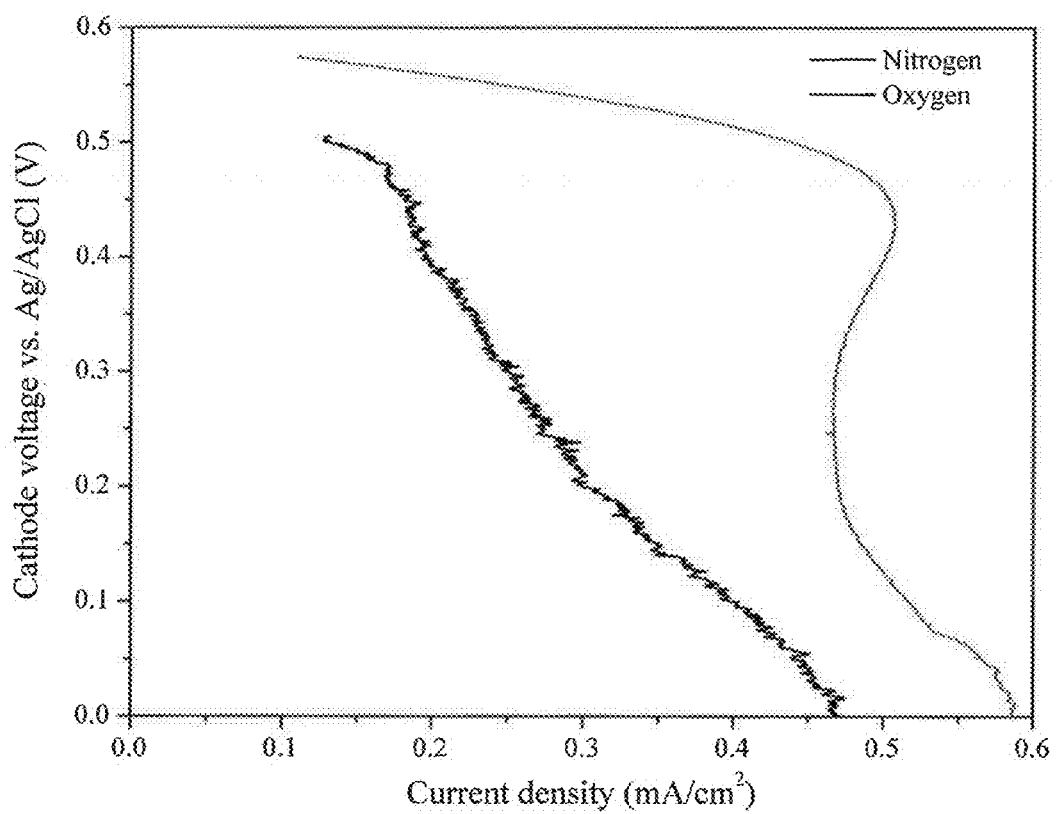
FIG. 6 shows one embodiment of the ink comprising the laccase enzyme for oxygen reduction and polarization curve of such electrode without and with presence of oxygen.

In one embodiment, the ink solution comprises enzyme lacasse. The ink of this example was prepared using the same protocol as described in Example 1 with the only difference being that the enzyme lacasse was substituted for glucose oxidase and provided biocatalyzed oxygen reduction. The electrode was then tested with a electrochemically technique of linear sweep voltametry against platinum counter electrode in 245 mM PBS buffer pH 5.8 that was (1) degassed with nitrogen and (2) oxygen saturated. FIG. 6 indicates differences in the reduction current with and without oxygen presence in the buffer solution. It demonstrates that multiple enzymes are active at the electrode and operates in direct electron transfer. Typical voltage operation range of such cathode is 0.4 to 0.5 V vs. sat. Ag/AgCl.

Example 7

This example shows that a battery comprising the ink of the present disclosure can be operated at elevated temperatures. A standard fuel cell was constructed using the glucose oxidase/ink modified anode of Example 1 and a Prussian Blue (PB) based cathode. Nafion membrane was used to separate the anodic and cathodic chambers. The anodic chamber was filled with fuel, as described in Example 2. Prior to filling the cell with fuel, both the fuel stock and the empty cell was placed in a +55° C. temperature controlled chamber for 15 minutes to come to operating temperature. The fuel was degassed with $N_2$ gas. After 15 minutes the cell was filled with fuel and left to continue equalization in the temperature controlled chamber for another 15 minutes. All testing was performed under the +55° C. operating conditions. Standard power curve and electrode polarization curves were measured on the cell as described in Example 2.

Figure 7A:
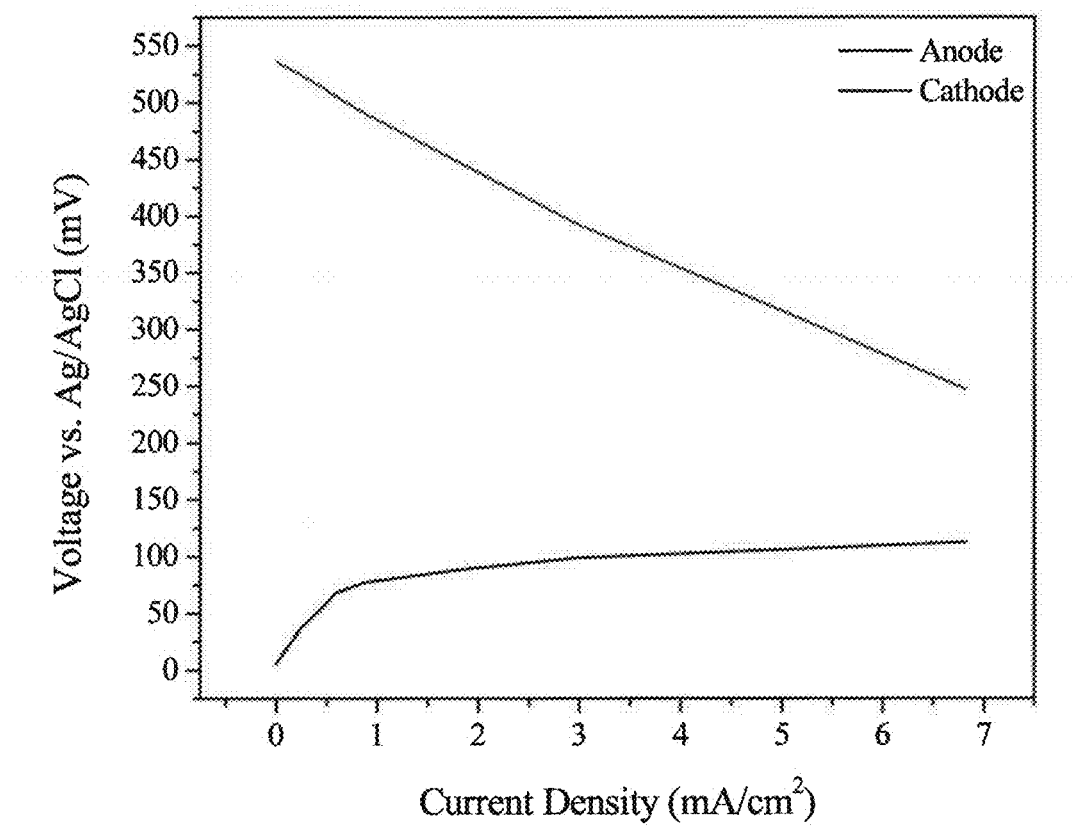
FIG. 7A shows polarization curves of the enzymatic anode of one embodiment of the ink when operated at 55 degrees Celsius; polarization curve for the cathode is also shown in FIG. 7B which shows power curve of such cell that is power density versus cell voltage.
Figure 7B:
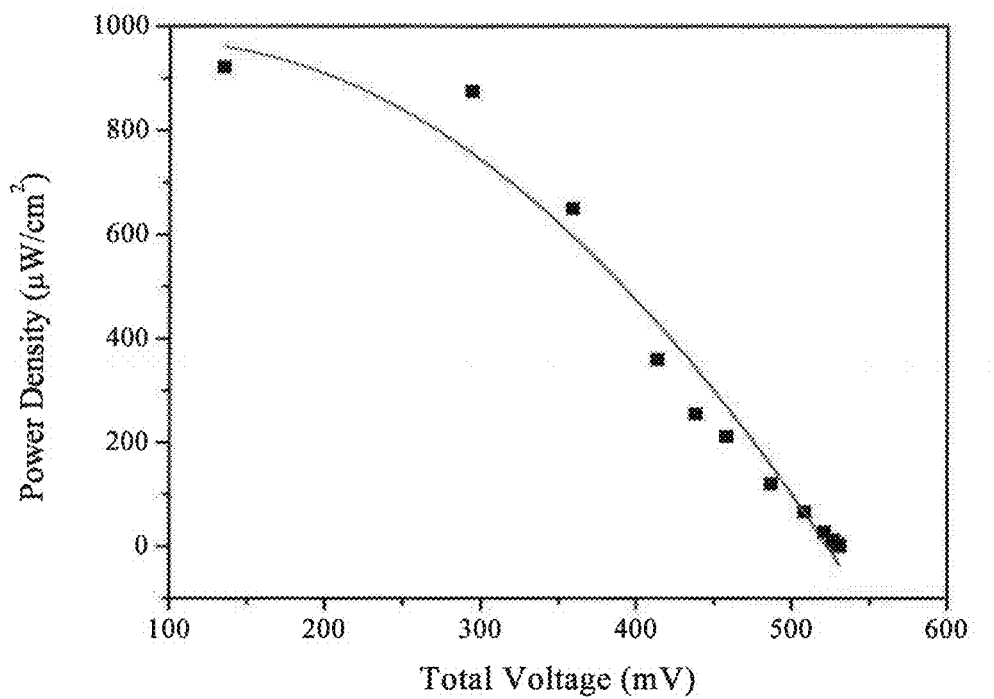
Figure 8:
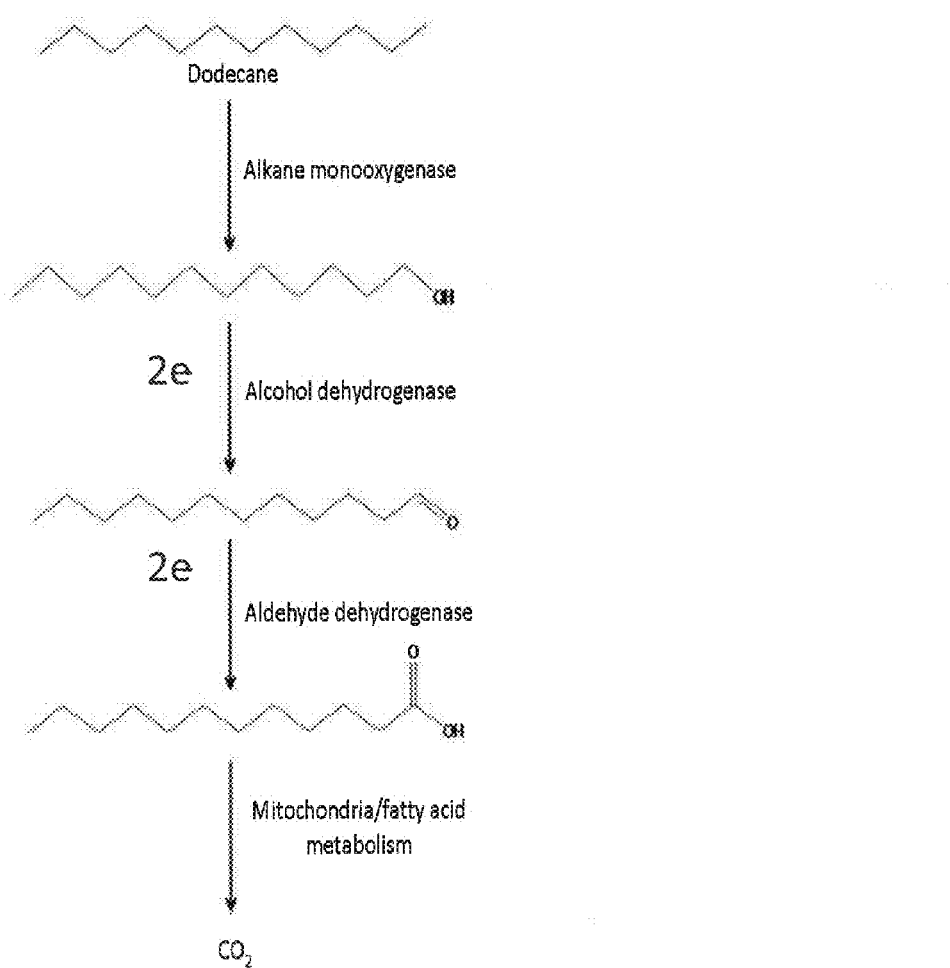
FIG. 8 shows one embodiment of the current invention wherein alkanes are first converted to their alcohol equivalents which are then further reduced to produce free electrons.

FIGS. 7A and 7B depict the polarization curves for the anode and cathode and power curve measured at elevated temperature of 55° C. The power curve in FIG. 7B shows a partial curve with the peak power density of 875 $\mu W \cdot cm^{-2}$ reached at 295 mV. This value of the peak power is very comparable to those achieved at room (+25° C.) temperature, suggesting that the ink and batteries containing the ink are stable and perform at elevated temperatures than are known in the art.

Example 8

To demonstrate catalytic activity of the enzyme alkane monoxygenase (AMO) towards alkanes spectroscopic assay testing was conducted. In this example UV-Vis spectrometry was employed to measure the absorbance of solution containing nicotinamide adenine dinucleotide (NADH, 0.15 mM) and octane (2 mM) suspended in Tris buffer (100 mM, pH 7.4) in the presence and absence of AMO. Stock solutions of NADH and octane were mixed together and diluted with Tris buffer to a final volume of 3 ml. A standard cuvette was filled with the above mentioned solution and placed in a UV-Vis spectrophotometer. The absorbance of solution was monitored as a function of time at 340 nm wavelength. FIG. 9 shows the results of the spectroscopic assay testing. The control (no enzyme) experiment showed a constant absorbance value of 0.9 over a time period of 300 seconds. The data for solution containing AMO showed a linear decrease in absorbance values over the same time period. This change in absorbance indicates the change in the solution chemical composition as AMO converts octane to octanol according to reaction schematic:

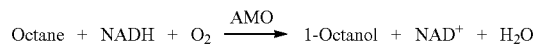

The steep slope of the enzymatic curve (red) indicates high catalytic activity of the enzyme towards the substrate.

Additional spectroscopic assay testing was performed employing hexane as substrate in order to validate enzymatic catalytic activity of AMO towards multiple substrates.

Similar procedure was followed for obtaining UV-Vis data for hexane assay and FIG. 10 depicts the results for this testing.

Furthermore, spectroscopic testing was performed in order to show sulphur tolerance of the AMO enzyme. Aliquots of potassium sulphate ($K_2SO_4$) were added to the already mentioned solution containing NADH and octane in Tris buffer. The final concentrations of sulphate were 5 and 10 mM respectively, which correspond to sulfur levels of approximately 1,000 ppm and 2,000 ppm. Absorbance measurements were taken and the data is presented in FIG. 11.

Example 9

In order to demonstrate power generation, a bi-enzymatic anode was coupled with oxygen reducing cathode in a fuel cell configuration. The anode comprised of AMO and alcohol oxidase (AOx) co-immobilized at the surface of carbon-based electrode in an electrically conductive ink.

The electrically conductive ink, used to modify the anode, comprised single wall COOH functionalized CNTs as the nanoscale conducting material, PEI as the binding agent, and AMO and AOx as the enzymes. To create the electrically conductive ink, the polymer was dissolved in a phosphate buffer solution by stirring in a ratio of 100-2000 µg/mL for several hours. After the solution was sufficiently mixed, CNTs were added to the mixture. In this example, single-walled CNTs with COOH functionalization were utilized. The CNT ratio was between 1-50 mg/mL and the mixing was accomplished via sonication with an ultrasonicator. Next, the enzyme and cross-linking agents are added to the solution. In this example, the cross linkers EDC and NHS were added along with enzymes AMO and AOx. To construct the electrode, a small volume of the electrically conductive ink solution was pipetted onto a carbon felt based electrode. The electrode was allowed to cure overnight at approximately 40 Celsius.

The cathode was prepared by mixing together Potassium ferricyanide and Iron (III) chloride in 1:2 mol ratios. Carbon black powder and carbon fibers were added to the mixture in 2:1 ratio by weight. Finally, 1-Butyl-3-methylimidazolium chloride (BMIMCl) ionic liquid was added to the dry mixture to make a thick paste. This paste was employed as the cathode for the fabrication of the fuel cell.

These electrodes were loaded into a custom designed graphite based fuel cell test assembly. A Nafion 112 membrane was used as a separator between the anode and the cathode chambers. The substrate (serving as the "fuel") comprised of 2% by vol. JP-8 (in 100 mM Tris buffer, pH 7.4) with 10 mM $NAD^+$ and 10 mM HQ used as mediators to improve electron transport. Constant load discharge technique was employed in the fuel cell testing, where a series or resistances from 30 MCl to 2×2 were applied to the cell for duration of 15 seconds per load and cell voltage and current were monitored as a function of time.

The maximum power was at ~10 ohms with a voltage of 0.4 V, current density of 7.5 $mA \cdot cm^{-2}$ and power density of 3 $mW \cdot cm^{-2}$ as shown in FIG. 12.

Example 10

The fundamental issue with employing medium to long chain alkanes as fuel in an aqueous system is the non-polar nature of the fuel, resulting in phase separation between the fuel and the conductive electrolyte. One method for overcoming this difficulty is to employ a carbon bond-cleaving enzyme lyase. This enzyme is capable of cleaving a C—C moiety from the alkane chain, resulting in shorter chain length and thus increasing alkane solubility in aqueous medium.

The overall theoretical process is presented below

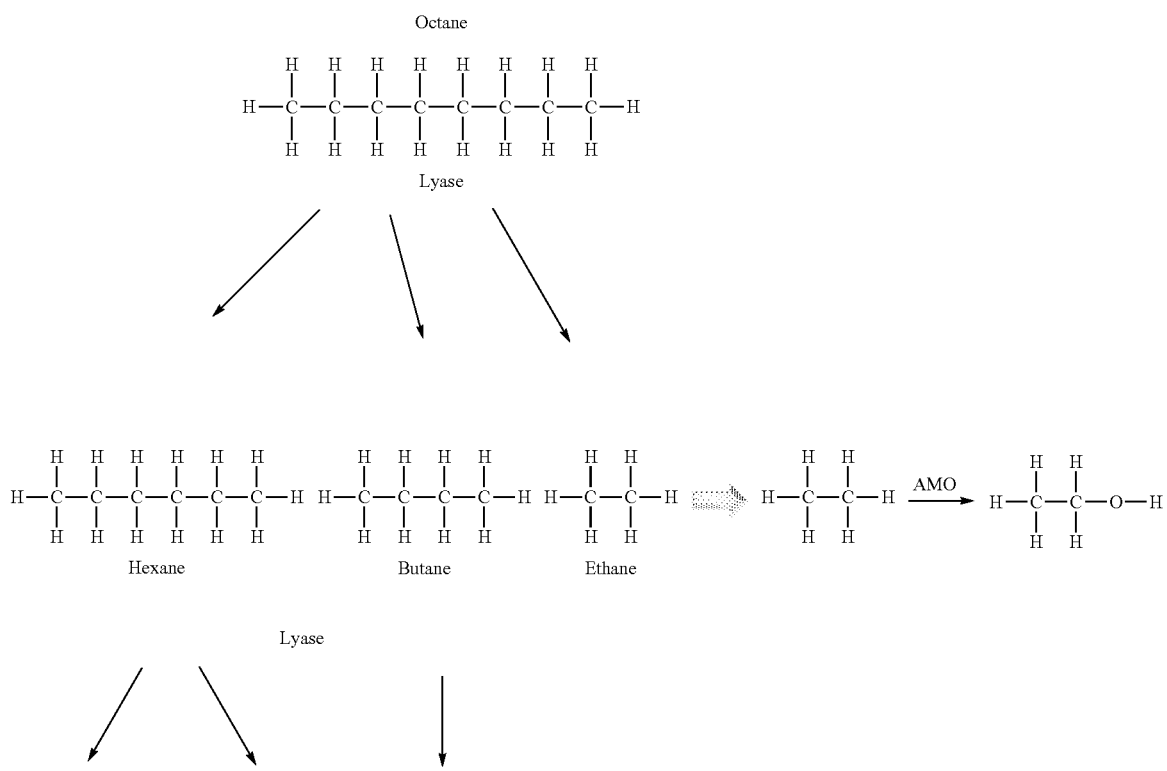

-continued

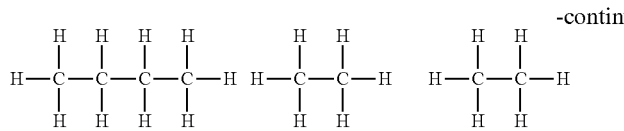

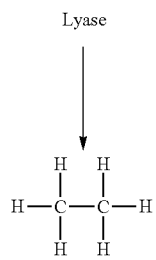

Aqueous solubility of alkanes increases with a decrease in carbon chain length. Thus the above mentioned process will result in increased miscibility of JP-8 with ionic electrolyte (buffer), enabling higher concentrations of fuel to be utilized and thus leading to higher power generation and longer run-times.

Although particular embodiments of the present disclosure have been described, it is not intended that such references be construed as limitations upon the scope of this disclosure except as set forth in the claims.

We claim:

1. A method of generating electricity from a non-polar substrate comprising at least a concentration of 100 ppm sulphur, said method comprising contacting the non-polar substrate with a plurality of enzymes, wherein at least one enzyme is non-electric current/potential enzyme that functions as a catalyst for a chemical reaction transforming a the substrate to a second substrate that can be used by one or more additional electric current/potential generating enzyme.

2. The method of claim 1 wherein the non-electric current/potential enzyme is selected from the group consisting of an alkane monooxygenase, an alkane hydroxylase, a membrane-bound particulate copper-containing enzymes, a soluble non-heme di-iron monooxygenase and a cytochrome P450 enzyme and the one or more additional electric current/potential generating enzymes is selected from the group consisting of alcohol oxidase, alcohol dehydrogenase, aldehyde dehydrogenase and aldehyde oxidase.

3. The method of claim 1 wherein said method generates at least 1 µW/cm$^2$.

4. The method of claim 1 wherein said non-polar substrate is a $C_3$-$C_{16}$ hydrocarbon.

5. The method of claim 3 wherein said non-polar substrate is selected from the group consisting of JP-8 fuel, JP-5 fuel, JP-4 fuel, methane, butane, propane, hexane, octane and diesel fuel.

6. The method of claim 4 comprising adding lyase to said substrate.

7. The method of claim 1 wherein the substrate comprises at least a concentration of 500 ppm sulphur.

8. The method of claim 1 wherein the substrate comprises at least a concentration of 1,000 ppm sulphur.

9. A method of generating electricity from a substrate selected from the group consisting of JP-8 fuel, JP-5 fuel, JP-4 fuel, hexane, methane, butane, propane, octane or diesel fuel, wherein said substrate comprises at least 100 ppm sulfur, said method comprising:
    contacting the non-polar substrate with a plurality of enzymes, wherein at least one enzyme is non-electric current/potential enzyme that functions as a catalyst for a chemical reaction transforming the substrate to a second substrate that can be used by one or more additional electric current/potential generating enzymes.

10. The method of claim 9 wherein the non-electric current/potential enzyme is selected from the group consisting of an alkane monooxygenase, an alkane hydroxylase, a membrane-bound particulate copper-containing enzymes, a soluble non-heme di-iron monooxygenase and a cytochrome P450 enzyme.

11. The method of claim 10 wherein the one or more additional electric current/potential generating enzymes is selected from the group consisting of alcohol oxidase, alcohol dehydrogenase, aldehyde dehydrogenase and aldehyde oxidase.

12. The method of claim 11 wherein said method generates at least 1 µW/cm$^2$.

13. The method of claim 9 wherein the substrate comprises at least a concentration of 500 ppm sulphur.

14. The method of claim 9 wherein the substrate comprises at least a concentration of 1,000 ppm sulphur.

* * * * *